United States Patent [19]

de Cooker

[11] 4,112,232
[45] Sep. 5, 1978

[54] PROCESS FOR PREPARING CYANURIC ACID

[75] Inventor: Mario G. R. T. de Cooker, Sittard, Netherlands

[73] Assignee: Stamicarbon, B.V., Geleen, Netherlands

[21] Appl. No.: 834,664

[22] Filed: Sep. 19, 1977

[30] Foreign Application Priority Data

Sep. 23, 1976 [NL] Netherlands .......................... 7610556

[51] Int. Cl.$^2$ .......................................... C07D 251/32
[52] U.S. Cl. .................................................... 544/192

[58] Field of Search ......................................... 544/192

[56] References Cited

U.S. PATENT DOCUMENTS 3,956,299  5/1976  den Otter et al. ................... 544/192

Primary Examiner—John M. Ford
Attorney, Agent, or Firm—Cushman, Darby & Cushman

[57] ABSTRACT

An improved process for preparing cyanuric acid by heating urea or biuret or a mixture thereof in a solvent to produce a cyanuric acid product of high purity.

12 Claims, 1 Drawing Figure

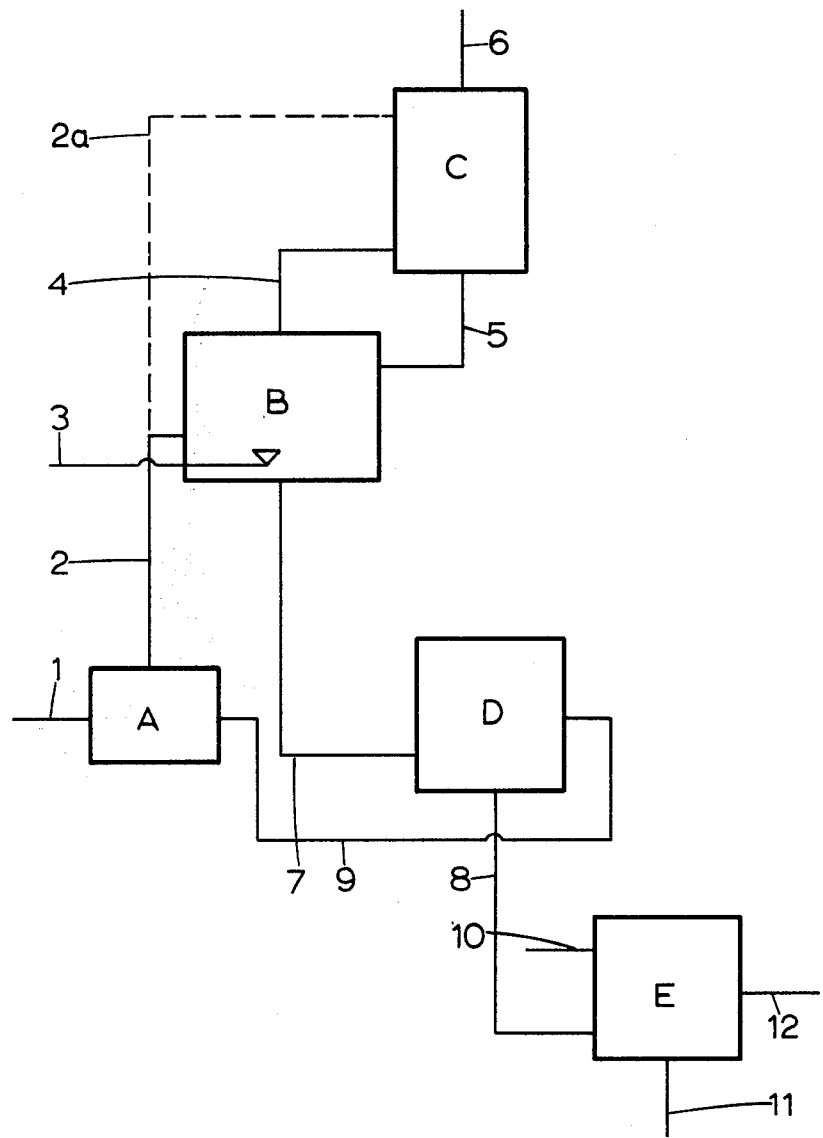

PROCESS FOR PREPARING CYANURIC ACID

BACKGROUND OF THE INVENTION

This application is related to Netherlands Pat. application No. 7610556, filed Sept. 23, 1976, the entire disclosure of which is hereby incorporated by reference.

The present invention relates to a process for preparing cyanuric acid by heating urea, biuret or a mixture of urea and biuret in a solvent to produce a pure cyanuric acid product with a low content of the by-products ammelide and ammeline.

Cyanuric acid is used as an intermediate in the preparation of other chemical compounds, e.g., the preparation of chlorocyanuric acid which is used in dry bleach compositions and detergents by direct chlorination of cyanuric acid in alkaline solution, and the production of resins.

The production of cyanuric acid from urea or biuret is known. The basic steps consist of first heating urea or biuret for several hours. This results in deamination of the urea and the formation of cyanuric acid:

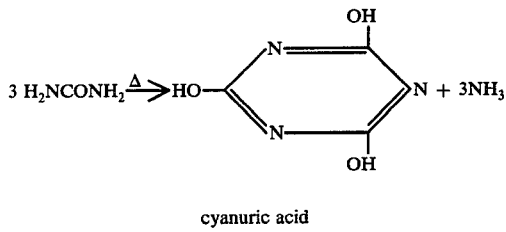

cyanuric acid

The reaction, however, is not as simple as the equation suggests. When urea or biuret is heated, it goes through several states before it is converted to cyanuric acid. Initially, the starting material melts to form a free-flowing liquid. As the heating continues, the reaction mass thickens and finally solidifies. However, at this point, the reaction is not complete. The reaction mass still contains significant amounts of urea, biuret, and triuret, which require additional heating to convert them to cyanuric acid. The additional heating is difficult because of the poor heat-transfer characteristics of the reaction mass. If the reaction mass is heated to too high a temperature, the yield of cyanuric acid product decreases due to depolymerization of the product. Another problem with the reaction is that the reaction product strongly adheres to the walls of the reactor and is removed with great difficulty.

Several methods, have been proposed to overcome these problems. For example, it has been proposed to run the reaction in certain high-boiling organic solvents. This and other proposed methods of overcoming the above-discussed problems are mentioned in the article "Triazinetriol" in the *Kirk-Othmer Encyclopedia of Chemical Technology, Second Edition*, Volume 20, pages 662 to 671, the entire disclosure of which is hereby incorporated by reference.

Many organic solvents have been proposed for use in running the reaction to convert urea or biuret to cyanuric acid. Examples of solvents which have been proposed include tetra (lower) alkyl ureas such as tetramethyl urea and tetraethyl urea; phenolic solvents such as cresol, xylenol, and chlorocresols; substituted amides such as dimethylformamide, dibutylformamide, and dimethylacetamide; glycol ethers; and urethanes, such as 5-methyl-2-oxazolidinone. The use of such solvents is disclosed in Netherlands Pat. application No. 74.05629 which is available for public inspection. However, each of the proposed organic solvents has its own disadvantages, particularly the presence of organic impurities in the cyanuric acid product.

It is a particular disadvantage of prior processes that the organic impurities produced in the cyanuric acid product are difficult to remove. However, the removal of such organic impurities is required for various applications of cyanuric acid. For example, ammeline and ammelide are formed as by-products in the preparation of cyanuric acid from urea, and are considered impurities in the cyanuric acid product. Typically, prior processes for preparing cyanuric acid from urea using no solvent produce as much as 20–30% impurities consisting mostly of ammelide and ammeline, with minor amounts of melamine, biuret, urea and triuret (*Kirk-Othmer Encyclopedia*, supra). Ammeline and ammelide are very undesirable by-products because they interfere in some important applications of cyanuric acid. Consequently, the ammeline and ammelide content of cyanuric acid may be required to be on the order of 1% by weight. It is common practice to purify crude cyanuric acid containing ammeline and ammelide by treating the crude acid with a strongly acid aqueous solution, so that the ammeline and ammelide are hydrolyzed into cyanuric acid. However, such a hydrolysis step is expensive, so that it would be very desirable to avoid it. Cyanuric acid obtained by prior art processes wherein an organic solvent is used contains normally besides ammelide and ammeline also traces of the solvent as organic impurities which are difficult to remove.

SUMMARY OF THE INVENTION

Briefly, in accordance with the invention, cyanuric acid is prepared by heating urea of biuret or a mixture thereof in a molten salt of an alkali or alkaline earth metal or a mixture of such salts, as a solvent. Any alkali or alkaline earth metal salt which has a sufficiently low melting point in the presence of urea or biuret or a mixture thereof may be used, provided that it is sufficiently inert under the reaction conditions to produce cyanuric acid. It is a particular advantage of the process of the present invention that it produces a pure cyanuric acid product with a low content of the by-products ammelide and ammeline.

It is therefore an object of the present invention to provide a process for preparing cyanuric acid by heating urea or biuret or a mixture thereof in a solvent of a molten salt of an alkali or alkaline earth metal, or a mixture of such molten salts.

Another object of the present invention is to provide a process for preparing cyanuric acid by heating urea or biuret or a mixture thereof in a molten salt solvent to produce cyanuric acid with a low content of ammelide and ammeline.

Another object of the present invention is to provide a process for preparing cyanuric acid by heating urea or biuret or a mixture thereof in a molten salt solvent containing an alkali or alkaline earth metal salt, or a mixture of such salts, and up to 50% by weight of one or more salts other than an alkali or alkaline earth metal salt.

Another object of the present invention is to provide a process for preparing cyanuric acid by heating urea or biuret or a mixture thereof in a molten salt solvent containing an alkali or alkaline earth metal, or a mixture of such salts, and up to 50% by weight of an ammonium salt derived from the same acid as the alkali or alkaline earth metal salt.

Other objects of the present invention will be apparent from the description of the invention which follows.

DESCRIPTION OF THE DRAWING

The process according to the present invention may be carried out either batchwise, or continuously. The drawing illustrates an example of a continuous process according to the invention.

Urea or biuret or a mixture thereof is passed through conduit 1 into dissolving vessel A, in which the urea, biuret or a mixture thereof is dissolved in a molten salt solvent containing at least one molten salt of an alkali or alkaline earth metal. The resulting solution flows through conduit 2 to the reaction vessel B, which is a gas-liquid contactor where the conversion into cyanuric acid is effected. If desired, a stripping gas such as nitrogen, or a condensable stripping additive such as xylene, or a mixture thereof, may be fed to reaction vessel B through conduit 3. A gaseous mixture containing ammonia, which is produced together with cyanuric acid, leaves reaction vessel B through conduit 4 and is fed to condenser C. The gaseous mixture leaving reaction vessel B may also contain vapors of any volatile salt present in the molten salt solvent (e.g., an ammonium salt vapor) and may also contain a stipping gas (e.g., xylene), if one is used.

Condenser C will condense any condensable stripping additive present in the gaseous mixture, and return it to reaction vessel B through conduit 5. Condenser C may also be a scrubber, in which the scrubbing liquid is preferably a solution of urea, or biuret, or a mixture thereof in the molten salt solvent used. When condenser C is a scrubber, the scrubbing solution is supplied to condenser C through conduit 2a. If the molten salt solvent used in the reaction contains a volatile salt such as an ammonium salt, the gaseous mixture fed to condenser C will contain vapors of the volatile salts. These vapors can be washed from the gaseous mixture by means of an aqueous liquid, such as water. Any ammonia which is removed by the washing liquid can be recovered by desorption, e.g., by stripping.

Uncondensed gas leaves condenser C through conduit 6. This uncondensed gas consists of substantially pure ammonia or a mixture of ammonia and stripping gas from which the ammonia can be easily recovered. If no condensable stripping additive has been used in reaction vessel B, and if no volatile salt component is used in the molten salt solvent, condenser C may be omitted.

A suspension of cyanuric acid in molten salt, flows from reactor vessel B through conduit 7 to separator D. In separator D, the cyanuric acid is separated from the molten salt by filtration, precipitation, decantation, centrifugation, or by another suitable separatory method. The solid cyanuric acid product is passed through conduit 8 to washer E, where it is washed with washing liquid supplied through conduit 10. The washing liquid used may, for example, be water, which leaves washer E through conduit 11. The washing liquid leaving washer E contains solvent salt, unconverted urea, and or biuret, and some cyanuric acid. If desired, these substances can be separated from the washing liquid and returned to the reaction system. Pure cyanuric acid is discharged through conduit 12.

If desired, the solid cyanuric acid product leaving separator D through conduit 8 may be subjected to a conventonal acid hydrolysis, e.g., with nitric acid, in order to hydrolyze the by-products ammelide and ammeline into cyanuric acid. The hydrolyzed cyanuric acid product continues to pass through conduit 8 to washer E, where it is treated as described above.

The mother liquor which is separated in separator D from the solid cyanuric acid product often still contains unconverted urea and or biuret, and is saturated with cyanuric acid. This mother liquor is passed through conduit 9 to dissolving vessel A.

At the beginning of the continuous process, a given amount of molten salt is put in reactor vessel B. This molten salt solvent keeps recycling, and any losses may be made up through conduits (not shown) located in the system, preferably at dissolving vessel A.

DETAILED DESCRIPTION OF THE INVENTION

The present invention provides a process for preparing cyanuric acid by heating urea or biuret or a mixture thereof in a molten salt solvent. The molten salt solvent according to the present invention may be any salt of an alkali or alkaline earth metal, or a mixture of two or more of such salts, that has a sufficiently low melting point to dissolve the other components of the reaction mixture such as urea or biuret without thermal decomposition, and which is sufficiently inert under the reaction conditions not to react with the other components of the reaction mixture. The molten salt solvent may also have a minor amount of another salt, i.e., not an alkali or alkaline earth metal salt, preferably derived from the same acid. In accordance with the present invention, this "minor amount" of another salt is at most 50% by weight of another salt.

Salts of sodium and potassium are particularly suitable alkali metal salts for use in the present invention, although other alkali metal salts, such as salts of lithium, may also be used. Salts of magnesium and calcium are particularly suitable alkaline earth metal salts for use in the present invention, although salts of other alkaline earth metals such as strontium and barium may also be used in the practice of the present invention. Ammonium salts are particularly preferred for use as the salt other than an alkali or alkaline earth metal salt in the practice of the present invention.

As used in the present application, the alkali metals include the elements of Group 1a of the "Periodic Table of the Elements" published in the *Handbook of Chemistry & Physics*, 47th Ed., except hydrogen, and the alkaline earth metals are the elements of Group 2a of the same "Periodic Table of the Elements".

According to the present invention, the alkali or alkaline earth metal salts used are derived from an inorganic or an organic acid. Preferred inorganic acids include hydrochloric acid, sulfuric acid, phosphoric acid, and nitric acid. Preferred organic acids include alifatic carboxylic acids, particularly fatty acids with up to 18 carbon atoms per molecule the most preferred inorganic acid from which salts useful in the molten salt solvent of the present invention may be derived in nitric acid. Preferably, the salts used to form the molten salt solvent in the practice of the present invention are free of water.

Examples of salts which are especially suitable for use in the practice of the present invention as components of the molten salt solvent include sodium nitrate, potassium nitrate, mixtures of sodium and potassium nitrate, mixtures of sodium nitrate, potassium nitrate and ammonium nitrate, mixtures of sodium nitrate, potassium nitrate and calcium nitrate, etc. It is preferred that the salt mixtures have, at least approximately, the eutectic composition. In the practice of the present invention a particularly preferred salt mixture is the eutectic mixture of sodium nitrate and potassium nitrate, which may also optionally contain either ammonium nitrate or calcium nitrate, or mixtures of ammonium nitrate and calcium nitrate. To obtain a sufficiently low melting point for use in the present invention, mixtures of sodium nitrate and potassium nitrate preferably have $NaNO_3:KNO_3$ weight ratios between 20:1 and 1:11. If ammonium nitrate, calcium nitrate or a mixture of ammonium nitrate and calcium nitrate is present in addition to sodium nitrate and potassium nitrate, suitable weight ratios of $NaNO_3:KNO_3:(NH_4NO_3$ and/or $Ca(NO_3)_2)$ are between (47 to 2):(1 to 22):(2 to 47).

In the process according to the present invention, it is advantageous to lower the ammonia concentration in reaction vessel B, i.e., the reaction vessel in which the conversion into cyanuric acid is effected. It will be remembered that the conversion of three moles of urea produces one mole of cyanuric acid and three moles of ammonia. The ammonia concentration may be reduced in the reaction vessel B by any known method. For example, the ammonia concentration may be lowered by stripping by means of a stripping gas such as air, nitrogen or carbon dioxide. Use may also be made of stripping or boiling additives that are fed to the reactor in the liquid state such as aliphatic, aromatic or mixed aliphatic-aromatic hydrocarbons. Suitable liquid stripping or boiling additives include hydrocarbons containing from about 3 to about 12 carbon atoms per molecule, such as cyclohexane, toluene, or a xylene. The ammonia concentration in the reactor may also be lowered by reducing the pressure above the reaction system, i.e., by conduction the conversion to cyanuric acid under less than atmospheric pressure.

The reaction temperature, i.e., the temperature at which urea, biuret or a mixture thereof is converted into cyanuric acid in a molten salt solvent in the practice of the present invention, usually ranges between about 150° and about 350° C., preferably between about 170° C. and about 280° C., and most preferably between about 175° C. and about 230° C. As the reaction temperature is raised, the reaction proceeds more quickly. However, as the reaction temperature is raised, the amount of undesired by-products, such as ammelide and ammeline, increases. Furthermore, increasing the reaction temperature increases the rate of decomposition of the molten salt solvent used in the process of the present invention.

The reaction pressure used in the practice of the present invention may range between about 0.01 and about 10 atmospheres. Preferably, the reaction pressure used in the practice of the present invention is between about 0.5 and about 2 atmospheres. Most preferably, the reaction pressure used in the practice of the present invention is approximately atmospheric pressure. When the ammonia concentration in the reaction vessel is lowered by conducting the reaction at less than atmospheric pressure, it is preferred to use a reaction pressure between about 0.01 atmospheres and a pressure just below atmospheric pressure. Most preferably, when ammonia is removed from the reaction vessel by conducting the reaction at less than atmospheric pressure, a reaction pressure between about 0.01 and about 0.25 atmospheres is used.

The reaction time used in the practice of the present invention is of course dependent on the temperature, but preferably ranges between about 5 minutes and about 4 hours. Preferably, the reaction time used is between about 15 minutes and about 2 hours.

The concentration of urea, biuret or a mixture of urea and biuret in a molten salt solution prior to conversion to cyanuric acid is preferably not too high. Concentrations of urea, biuret or mixtures of urea and biuret up to about 500 grams per kilogram of solution are preferred in the practice of the present invention. Higher concentrations of urea, biuret or mixtures of urea and biuret may be used in the practice of the present invention, but these tend to increase the amount of ammelide in the cyanuric acid product produced. At very low concentrations, biuret or mixtures of urea and biuret, a very pure cyanuric acid product is obtained, although the costs per unit product obtained are high. Therefore, in order to obtain a pure cyanuric acid product at a suitable price, it is preferred that the starting concentration of urea, biuret or mixtures of urea and biuret be in the range between about 150 and about 500 grams per kilogram of solution.

In the practice of the present invention, when urea, biuret or a mixture of urea and biuret is heated in a molten salt solvent as described above, a cyanuric acid product is formed which is relatively insoluble in the molten salt solvent and forms a crystalline precipitate in the molten salt solvent. The cyanuric acid product may be separated from the molten salt solvent by conventional techniques.

In the practice of the present invention, it is found that a pure cyanuric acid product with a low content of ammelide and ammeline is obtained particularly when the molten salt solution used contains ammonium nitrate. Therefore, molten salt solvents containing ammonium nitrate are particularly preferred in the practice of the present invention.

The invention will now be elucidated in more detail in the following Examples.

EXAMPLES I TO V

A mixture of the specified amount of urea and the specified amounts of the salts indicated was heated from room temperature to the specified reaction temperature in a 250-ml flask in Examples I to IV (a 500-ml flask was used in Example V) with proper stirring, while the specified amount (expressed in normal liters, abbreviated Nl, per hour of stripping gas was passed through the reaction flask. Nitrogen was used in the stripping gas in Examples I, II, IV and V. Ammonia was used as the stripping gas in Example III. The reaction time was measured from the time the reaction temperature was reached. At the end of the reaction time specified, the reaction mixture was rapidly cooled to room temperature by means of ice water. Salts and unconverted urea were dissolved in water, the cyanuric acid was filtered off, washed with water and dried. The percentage of ammelide (including ammeline) was calculated with respect to the total amount of cyanuric acid formed.

| Ex. | Urea (g) | NH$_4$NO$_3$ (g) | NaNO$_3$ (g) | KNO$_3$ (g) | Ca(NO$_3$)$_2$ (g) | Reaction Time (min) | Temperature (°C) | Nitrogen (Nl/h) | Urea Conversion (%) | Ammelide (% by Weight) |
|---|---|---|---|---|---|---|---|---|---|---|
| I | 20.7 | — | 67.0 | 23.0 | — | 20 | 225 | 75 | 75 | 29.0 |
| II | 31.3 | — | 67.9 | 23.4 | — | 18 | 230 | about 80; not measured* | 40 | 21.0 |
| III | 50.0 | — | 50.0 | — | — | 60 | 200 | 80* | 44 | 16.5 |
| IV | 27.5 | 17.0 | 40.3 | 42.7 | — | 60 | 60 | 100 | 75 | 1.15 |
| V | 37.5 | — | 23.8 | 58.8 | 42.5 | 60 | 200 | 170 | 50 | 7.9 |

*Ammonia instead of nitrogen.

Thus, it is apparent that there has been provided in accordance with the invention, a process for preparing cyanuric acid by heating urea, or biuret or a mixture thereof in a molten salt solvent that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the following claims.

What is claimed is:

1. A process for preparing cyanuric acid, comprising: heating a solution of urea, biuret or a mixture of urea and biuret in a molten salt solvent comprising at least one alkali metal salt or alkaline earth metal salt, and forming cyanuric acid and ammonia in said solution.

2. The process according to claim 1 wherein said alkali metal salt or alkaline earth metal salt is an alkali metal nitrate or an alkaline earth metal nitrate.

3. The process according to claim 2 wherein said molten salt solvent is a mixture of sodium nitrate and potassium nitrate with a NaNO$_3$:KNO$_3$ weight ratio between 20:1 and 1:11.

4. The process according to claim 1 wherein said molten salt solvent contains at least one salt other than an alkali metal salt or alkaline earth metal salt, said salt being present in an amount up to 50% by weight based on the total weight of the solvent.

5. The process according to claim 4 wherein said inorganic salt is an ammonium salt derived from the same acid as said alkali metal salt or alkaline earth metal salt.

6. The process according to claim 5 wherein said molten salt solvent is a mixture of sodium nitrate, potassium nitrate and ammonium nitrate.

7. The process according to claim 4 wherein said molten salt solvent is a mixture of sodium nitrate, potassium nitrate, and a nitrate selected from the group consisting of ammonium nitrate, calcium nitrate, and a mixture of ammonium nitrate and calcium nitrate, with a NaNO$_3$:KNO$_3$:(NH$_4$NO$_3$ and/or CA (NO$_3$)$_2$) weight ratio of between (47–2):(1–22):(2–47).

8. The process according to claim 1 including heating said solution of urea, biuret or a mixture of urea and biuret in said molten salt solvent at a temperature from 150° C to 350° C.

9. The process according to claim 1 including heating said solution of urea, biuret or a mixture of urea and biuret in said molten salt solvent at a temperature from 175° C to 230° C.

10. The process according to claim 1 including reducing ammonia during the reaction the concentration of said ammonia in said solution containing cyanuric acid.

11. The process according to claim 10 wherein ammonia is removed from said solution containing cyanuric acid by stripping with a stripping gas, a stripping additive or a mixture of a stripping gas and a stripping additive.

12. The process according to claim 10 wherein ammonia is removed by heating said solution of urea, biuret or a mixture of urea and biuret in a molten salt solvent under less than atmospheric pressure.

* * * * *